United States Patent [19]

Okita

[11] 4,104,394
[45] Aug. 1, 1978

[54] METHOD FOR DIAMETRICALLY EXPANDING THERMALLY CONTRACTIVE PTFE RESIN TUBE

[75] Inventor: Koichi Okita, Osaka, Japan

[73] Assignee: Sumitomo Electric Industries, Ltd., Osaka, Japan

[21] Appl. No.: 750,319

[22] Filed: Dec. 14, 1976

[30] Foreign Application Priority Data

Dec. 15, 1975 [JP] Japan ............................. 50-149718
Dec. 24, 1975 [JP] Japan ............................. 50-155226
Sep. 22, 1976 [JP] Japan ............................. 51-114006
Sep. 11, 1976 [JP] Japan ............................. 51-134853

[51] Int. Cl.² ............................................. B29C 17/07
[52] U.S. Cl. ......................................... 264/89; 264/95; 264/108; 264/127; 264/209; 264/211; 264/230; 264/DIG. 71
[58] Field of Search ............... 264/89, 88, 95, 209, 264/127, 230, 108, 327, DIG. 71, 310, 312

[56] References Cited

U.S. PATENT DOCUMENTS

| | | | |
|---|---|---|---|
| 2,456,621 | 12/1948 | Cheney | 264/127 |
| 2,791,806 | 5/1957 | Tordella | 264/127 |
| 2,821,155 | 1/1958 | Seckel | 264/230 |
| 3,008,187 | 11/1961 | Slade | 264/127 |
| 3,086,242 | 4/1963 | Cook et al | 264/95 |
| 3,225,129 | 12/1965 | Taylor et al. | 264/230 |
| 3,370,112 | 2/1968 | Wray | 264/22 |

Primary Examiner—Jeffery R. Thurlow
Attorney, Agent, or Firm—Sughrue, Rothwell, Mion, Zinn and Macpeak

[57] ABSTRACT

An unsintered tube of extruded ptfe resin is heated above its melting temperature of 327° C, a positive pressure is established within the tube relative to the external pressure thereon to radially expand it, and the pressure is maintained until the tube is cooled below its melting point and set. Such a tube demonstrates superior strength and crack resistance when it is thereafter radially contracted around a core member by reheating, and its longitudinal shrinkage is minimized.

20 Claims, 7 Drawing Figures

METHOD FOR DIAMETRICALLY EXPANDING THERMALLY CONTRACTIVE PTFE RESIN TUBE

BACKGROUND OF THE INVENTION

This invention relates to a diametrical expansion treatment of polytetrafluoroethylene (ptfe) resin tubes, and more particularly to a method of manufacturing so-called contraction tubes having a memory function in which the tubes maintain their shapes at room temperature, but when heated above a certain threshold temperature their shapes are changed and returned back to their original shapes.

A manufacturing method in which, after being irradiated and suitably bridged, a mixture of theroplastic material and polyethylene, polyvinylchloride or neoprenesilicon is subjected to expansion treatment, to thereby function as a contraction tube, is taught by U.S. Pat. Nos. 3,086,242 and 3,370,112. Since an extruded pfte resin tube has a considerably high melting viscosity at a temperature above 327° C, by cooling it below 327° C under pressure a tube having the same contractivity can be obtained. However, in the extruded ptfe resin, crystalline particles are arranged in the extrusion direction but not in the lateral direction, as is well known in the art. This orientation characteristic remains even after heat treatment at a temperature higher than 327° C. Therefore, when in order to radially expand the extruded tube, the outer surface of the tube is subjected to a negative or vacuum pressure and high pressure air is introduced into the inside of the tube, the tube frequently cracks in the longitudinal direction, and it is therefore difficult to manufacture long ptfe resin tubes.

This difficulty can be overcome to some extent by heat-treating the extruded tube without any pressure differential between the inner and outer surfaces thereof, and by radially expanding it at a temperature higher than 327° C with a positive pressure differential between the inner and outer surfaces. This method is not practical in a manufacturing operation, however. Further, if the tube contains a material which allows the contraction of the tube to an extent that a residual stress remains, when the tube is heated cracks are generated in the axial direction of the tube. The frequency of occurrence of and magnitude of the cracks depends on the magnitude of the residual stress. For instance, when the tube is completely contracted to its original diameter, the residual stress becomes zero, and accordingly no crack occurs.

However, in the use of a thermally contractive tube, some residual stress frequently remains. If such residual stress is completely eliminated, the adhesivity between the covering tube and the core material becomes extremely poor. Thus, the conventional ptfe resin tube has a number of drawbacks.

SUMMARY OF THE INVENTION

An object of the present invention provide a method of manufacturing improved tubes in which all of the above-described drawbacks have been eliminated.

In the method according to the invention, while an unsintered tube is sintered, the pressure applied to the outer surface thereof is reduced, and pressure is preferably applied to the inner surface thereof at more than 0.7 Kg/cm², whereby the tube is expanded by the differential pressure between the outer and inner surfaces of the tube. Thereafter, while the pressure applied to the inner surface of the tube is maintained, the tube is cooled down below the sintering temperature, whereby stable contractive tubes are continuously manufactured.

The unsintered tube employed in this method may be manufactured by the conventional paste extrusion method; however, as unsintered tubes of this type are liable to crack in the longitudinal direction, their use is limited. Therefore, when an unsintered tube employed in this invention is extruded, at least one of and preferably both the die and the mandrel for defining the outside and inside diameters of the tube are turned in opposite directions. As a result, the crystalline particles are oriented not only in the extrusion direction as in the conventional method, but also in a lateral or perpendicular direction, whereby the possibility of cracking the tube is greatly reduced.

The orientation of the crystalline particles is produced by the shearing force generated by the metal walls in the extrusion paste. By rotating at least one of the metal walls, the crystalline particles are also oriented in the lateral direction. In tubes of this type, the degrees of orientation of the crystalline particles in the extrusion and lateral directions can be equalized. Such a tube can thus be clearly distinguished from a conventional tube, which has significant anisotropy.

If a mixture of a "fine powder" resin and a liquid lubricant is subjected to an extrusion process, crystalline particle orientation is effected and at the same time fiber formation is effected, especially in the surface layer. Similar to the orientation of the crystalline particles, the direction of the fiber formation coincides with the extrusion direction. This fiber formation is closely related to the strength of the tube, and the strength of an unsintered tube depends completely on the fiber formation. More specifically, the tensile strength of a resin in which no fibers are formed is so low that it cannot be measured; however, the tensile strength of a resin in which fibers are formed is higher than 2 Kg/cm².

This effect of the fiber formation can be observed in a resin sintered at a temperature higher than 327° C. The fibrous tube is flexible and strong, and can be easily bent. On the other hand, the tube having no fiber formation cannot be bent without cracking. If an ordinary extruded sintered tube is bent, it is liable to crack in the longitudinal direction. This coincides with the fact that the thermally contractive tube is cracked when it is contracted to the extent that residual stress exists therein.

As described above, it is important that the ptfe resin is made fibrous in its unsintered state and the crystalline particles are oriented therein. This is peculiar to ptfe resin; that is, such a feature is not observed in other resins. This tendency is enhanced as the diameter of the tube is increased and its wall thickness is decreased.

In addition, the method according to this invention is characterized in that an unsintered tube is heated to a temperature higher than 327° C under atmospheric pressure, and before it is cooled down below 327° C it is expanded by providing a differential pressure between the inner and outer surfaces of the tube. In general, if an unsintered tube high in crystallization percentage (more than 93%) is heated above 327° C and then cooled, the crystallization decreases to 60 to 70%. If the tube thus treated is heated above 327° C and cooled again, the crystallization decreases to less than 50%, and its mechanical strength also decreases. Accordingly, in a method in which, similar to conventional method, a tube is manufactured by heating to a temperature higher than 327° C under atmospheric pressure, and the tube is then expanded by heating above 327° C again, the crystallization percentage and the mechanical strength are decreased. This is considered as one of the reasons why cracks are generated in the tube when it is used.

One of the specific features of this invention resides in the tube being heated above 327° C only once, to thereby expand it. As a result, according to the invention a thermally contractive tube in which cracks seldom occur can be obtained.

According to this invention, an unsintered tube is first produced by the paste extrusion method. A "fine powder" resin is suitable for the unsintered ptfe. A liquid lubricant which can wet the surface of the resin, and which can be removed by evaporation and extraction at a temperature lower than the decomposition temperature of the resin, can also be employed. Usually, a hydrocarbon oil such as mineral oil is employed.

A mixture of the resin and the liquid lubricant is then compressed and molded in advance, and is then loaded into a ram type extruder where it is extruded into a tube. To prevent the tube from cracking in the longitudinal direction when it is expanded, the mixture is heated. In this connection, the mandrel, and the die or die-land for defining the final shape of the tube should be heated to a temperature higher than the temperature of the mixture, preferably more than 50° C higher. This further enhances the fiber orientation in the longitudinal direction of the extruded tube, and accordingly the lateral strength of the tube is also increased.

Better results can also be obtained by using an extruder in which rotary drive means are coupled to the mandrel of a ram type extruder, while similar rotary drive means are also coupled to the die or die-land, such that at least one of and preferably both the mandrel and the die or die-land are rotated in opposite directions.

The most desirable conditions are as follows:
(a) the mixture is extruded while being heated,
(b) the temperature of the die or die-land is higher than that of the mixture, preferably more than 50° C higher, and
(c) fiber formation is generated in the lateral or perpendicular direction by rotating the mandrel and the die or die-land, to thereby prevent the occurrence of cracks in the tube when it is radially expanded or when it is contracted in use.

DETAILED DESCRIPTION OF THE PREFERRED EMBODIMENTS

Figure 1:
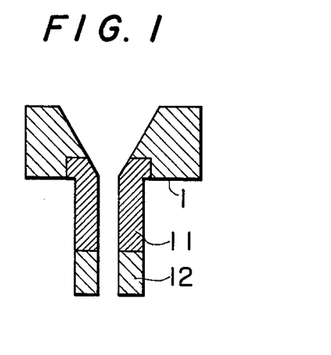
FIG. 1 is a longitudinal sectional front view showing a die assembly for regulating the outside diameter of a tube.

FIG. 1 shows a die adapted to regulate the outside diameter of a tube. The die may be made of a single block of material such as steel. In this case, the whole item shown in FIG. 1 is called a die. On the other hand, necessary parts fabricated separately may be assembled into the die. In this case, the assembly of a die 1 in a narrow sense and a die-insert 11 is called a die in a broad sense. Furthermore, the assembling parts may be subdivided. That is, the foot of the die-insert may be separately provided. The part corresponding to the foot of the die insert will be referred to as "a die-land 21".

In general, the definition of a die-land means the distance between the point where the upper tapered surface formed by drilling a metal block has the dimension of the final shape of a product and the tip end of the foot. However, the part 21 will be referred to as a die-land for convenience in description.

Figure 2:
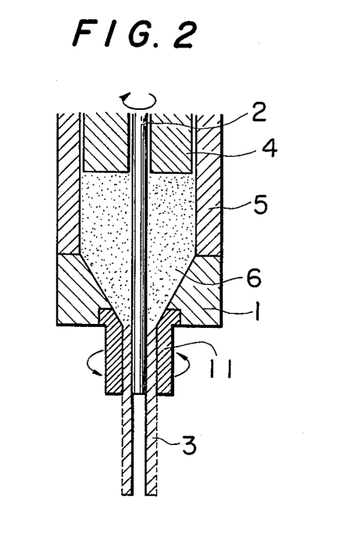
FIG. 2 is a longitudinal sectional front view illustrating a ramp type extruder for practicing this invention.

In a device shown in FIG. 2, an extrusion unit obtained by assembling the die 1 in a narrow sense and the die-insert 11 is combined with a mandrel 2, a ram 4 and a cylinder 5 to form a metal extrusion mold.

A material 6 molded under pressure in advance (hereinafter referred to as "a primary material or product 6" when applicable) is charged into the cylinder, and is formed into a tube 3 by the downward movement of the ram 4. If in this operation the mandrel 2 or the die-insert 11 is rotated, or more preferably the mandrel 2 and the die-insert 11 are both rotated in opposite directions while the primary material 6 is being extruded, the extruded tube 3 becomes fibrous not only in the extrusion direction but also in the direction perpendicular to the extrusion direction, that is, in two different directions owing to the shearing force generated by the rotating metal walls.

The degree of the fibrous state of the product in the direction perpendicular to the extrusion direction depends on the sectional area of the cylinder 5, the downward movement rate of the ram 4, the heating temperature, the shape of the mandrel 2, the opening angle of the die 1 and the die-insert 11, and the length of the die-land 21, and therefore cannot be represented by a simple numerical value. However, the degree of the fibrous state in question increases as the rotation of the die-insert 11 or the mandrel 2 increases.

The shearing force due to rotation is generated by the contact surfaces of the metal walls, namely, the die-insert 11 and the mandrel 2, and the primary material 6. However, the shearing forces generated by the part where the product is formed into the final shape and by the part through which the product passes thereafter are effective for making the tube 3 fibrous in the direction perpendicular to the extrusion direction, and the shearing force generated before the product is formed into the final shape is less effective for making the product fibrous in the direction perpendicular to the extrusion direction. On the other hand, when an excessively fibrous material is mixed with the material 6, the fibrous condition of the former material is different from the fibrous condition of the latter material obtained by the shearing forces caused by the metal surfaces of the die-insert 11 and the mandrel 2. Therefore, sufficiently fibrous layers and insufficiently fibrous layers are mixedly provided in the direction of thickness of the tube 3, and the tube has little strength in the interfaces of these layers. This means that the pipe is unstable in strength characteristic in the longitudinal direction thereof.

Thus, the fibrous-state formation in the extrusion direction is first effected until the sectional area of the material 6 being extruded is gradually reduced and finally the tube 3 having the final shape is formed, and then the fibrous-state formation in the tube 3 in the direction perpendicular to the extrusion direction is effected by the rotating shearing forces due to the die-insert 11 and the mandrel 2 without changing the sectional area of the tube 3 being extruded.

When only the mandrel 2 out of the metal walls adapted to regulate the final shape of the product is rotated, the direction of the fibers on the inner surface of the tube 3 has an angle with respect to the extrusion direction. This angle increases as the rotation of the mandrel increases and the extrusion rate decreases. On the other hand, when only the die-insert is rotated, the direction of the fibers on the outer surface of the tube 3 has a certain angle with the extrusion direction. If it is assumed that the rotation speed of the mandrel 2 is equal to that of the die-insert 11, the latter case where only the die-insert is rotated is more effective than the former case where only the mandrel 2 is rotated, because the contact area with the metal wall in the latter case is larger than that in the former case.

Figure 3:
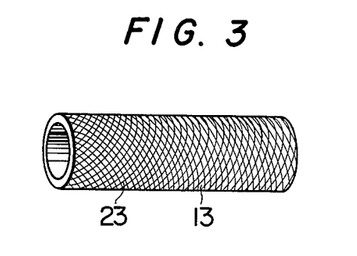
FIG. 3 is a perspective view showing the directions of fibers in an extruded tube.

When the die-insert 11 and the mandrel 2 are rotated in opposite directions, as for instance the die-insert 11 is rotated clockwise and the mandrel 2 is rotated counterclockwise, the directions of the fibers on the inner and outer surfaces of the tube 3 have angles with respect to the extrusion direction, respectively, while the angles of the directions of the fibers on the inner and outer surfaces of the tube increase as shown in FIG. 3 by way of example.

Figure 4:
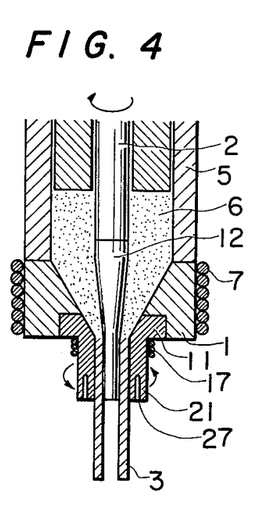
FIG. 4 is also a longitudinal sectional front view (partially omitted) showing a modified extruder according to the invention.
Figure 5:
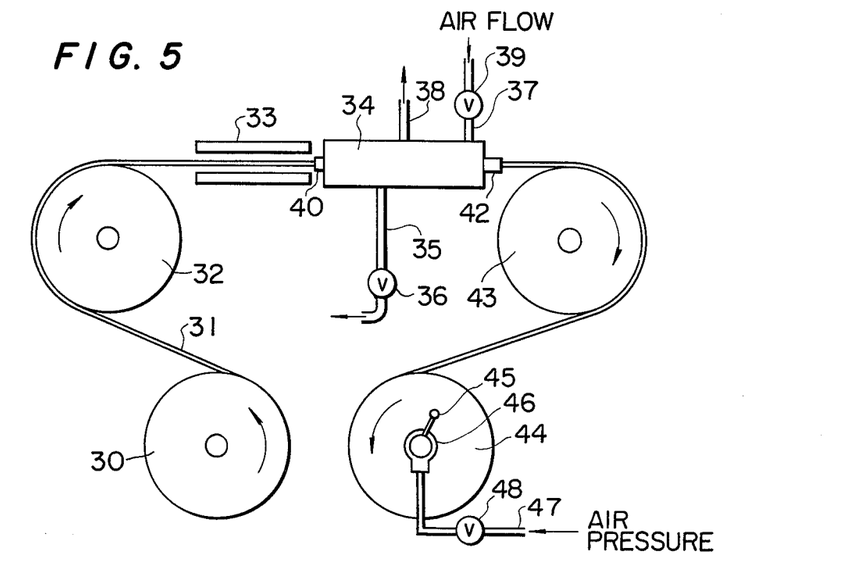
FIG. 5 shows a schematic side view of an apparatus for practicing the process of the invention.

In FIG. 3, the solid line 13 indicates the direction of the fibers on the outer surface of the tube 3, while the dotted line 23 indicates the direction of the fibers on the inner surface of the tube 3. A turning force or a turning shearing force of the metal wall adapted to determine the final shape of the product in which the sectional area in the extrusion direction is no longer changed induces the fibrous-state formation in the direction perpendicular to the extrusion direction. Therefore, a device in which the die-land 21 is rotated is shown in FIGS. 4 and 5. In each of the embodiments in FIGS. 4 and 5, as the length of the die-land 21 is increased, the effect to the fibrous-state formation in the perpendicular direction is increased. However, in the case where the length of the die-land 21 is decreased, the similar effect can be obtained by increasing the rotation speed of the die-land 21.

In order to accelerate the fibrous-state formation in the direction perpendicular to the extrusion direction, it is preferable to provide a die-land 21 whose opening diameter is about 2–10% smaller than the opening diameter of the die 1. However, in the embodiment in FIG. 4, if the opening diameter of the die-land 21 is reduced by 15% or more of the opening diameter of the die 1, part of the load pressure required for extrusion is applied directly to the die-land, as a result of which it is considerably difficult to keep the die 1 in close contact with the die-land 21. This problem is eliminated by providing a heater 7 for heating the material 6 and heaters 17 and 27 for heating the tube 3 having the final shape. The temperature of the tube 3 is made higher, preferably 50° C or higher, than the temperature of the material 6 by the heaters 17 and 27 so that upon formation of the tube 3 from the material 6, the tube 3 is subjected to thermal expansion. The fibrous-state formation in the direction perpendicular to the extrusion direction is accelerated in proportion to the degree of the thermal expansion.

If in addition to the mandrel 2, a core pin 12 is made as a metal wall for defining the inside diameter of the tube 3, it is possible to transmit the turning force of the mandrel 2 as the turning force of the core pin 12. This is suitable for changing the inside diameter of the tube 3.

All of the liquid lubricants employed in the conventional paste extrusion process can be used as the liquid lubricant in the method according to this invention. The blending quantity can be selected similarly as in the conventional paste extrusion process. That is, a variety of materials such as naptha, hydrocarbon oil such as white oil, aromatic hydrocarbon oil such as toluole, ketone, alcohol and ester can be employed. Usually, 10–30 parts of liquid lubricant is blended with 100 parts of resin. Furthermore, it is possible to blend various materials such as filler, metal powder, metallic acids, carbon, and glass fibers for the purpose of coloring, reinforcement, etc.

The mixture of unsintered polytetrafluoroethylene resin powder and liquid lubricant can be molded under pressure in advance completely similarly as in the conventional paste extrusion process.

The effects obtained when the die or the mandrel is rotated, will be described.

The extrusion of tubes, pipes and electrical wires frequently suffers from thickness deviation and center deviation. However, the thickness deviation and center deviation of the extruded product can be completely eliminated by rotating the mandrel or the wire guide tube from the start of the extrusion, because in the case of rotating the mandrel, the position thereof where the thickness deviation and center deviation are minimized under the static water pressure load coincides with the most stable position.

The static water pressure required for extrusion can be observed as the load pressure to the ram. However, when one or both of the die and mandrel start to rotate, the extrusion load pressure is decreased, that is, the extrusion load pressure is reduced to 70% of the extrusion load pressure obtained when the rotation speed is zero. This is due to the fact that the load pressure of about 30% is given by the rotating metal wall in order to change the paste-like mixture of the polytetrafluoroethylene resin powder and the liquid lubricant from the primary material to the final product, and the fact that while the paste-like mixture lowers the fluidity by orienting the fibers in one direction, or in the extrusion direction, the fluidity is improved by orienting the fibers in two directions, that is, in the extrusion direction and in the direction perpendicular to the extrusion direction.

If the rotation speed is further increased, the extrusion load pressure begins to increase, and finally becomes greater than the extrusion load pressure obtained when the rotation speed is zero.

This tendency is accelerated as the temperature of the premolded material is increased, and finally the extrusion becomes impossible. However, if the temperature of the insert die or the die-land is increased and the temperature of the premolded material is made lower than the increased temperature of the insert die or the die-land, the viscosity of the liquid lubricant can be decreased and a continuous extrusion can be carried out and the fibrous-state-making in the direction perpendicular to the extrusion direction is accelerated.

The working temperature is closely related to the degree of the fibrous state formation. In general, the fibrous state formation is accelerated as the working temperature increases. However, if the fibrous state formation is extremely advanced before the product has the final shape, it loses fluidity, as a result of which the extrusion becomes impossible. Therefore, the condition of heating the premolded material affects the fibrous state formation in the extrusion direction of the tube, while the condition of heating the insert die or the die-land mainly affects the fibrous state formation of the tube in the direction perpendicular to the extrusion direction.

By selecting these temperature conditions, products different in the degree of fibrous state formation in the two dimensional directions can be manufactured. In this connection, if the temperature difference is made to be 50° C or higher, uniform fibrous state formation can be obtained in the two different directions.

The condition of the fibers of unsintered resin arranged in the direction approximately perpendicular to the final extrusion direction can considerably improve the lateral strength and elongation of the pipe molded by extrusion. In the product formed by the conventional extrusion process, the fibrous state of resin is observed only in the extrusion direction as was described before, and the strength in the lateral direction is, in general, of the order of 0.01 Kg/mm$^2$, that is, it is so small that it is difficult to measure the strength. In addition, the elongation is less than 10%, and therefore the product will be readily cracked by slight deformation. On the other hand, in the product formed according to the process of this invention the fibrous state is observed both in the longitudinal and lateral directions. Although the strength is varied according to the reduction rate obtained when the product is extruded, it is not difficult to obtain a strength of 0.2 Kg/mm$^2$ and higher. Especially the elongation is remarkably improved to higher than 300%.

Conventional extruded products in the unsintered state must be handled with great care. For instance, thin wall pipes whose diameters are greater than 10 mm must be handled so that they are not bent and the walls are not cracked in the longitudinal directions by applying pressure in the diametrical directions. On the other hand, the pipes formed according to the process of the invention can withstand the bending force even if they are unsintered, and no longitudinal cracking is caused even if they are considerably deformed before sintering. Accordingly, defects which may be caused during the manufacturing process can be eliminated, and the unsintered products state can be bent to a certain degree, and therefore it is not always necessary to make a straight line from the extruder to the sintering furnace. Furthermore, where the product, such as covered electrical wires, is directed in several directions through pulleys for drying and sintering, no defect is caused even if it is bent when passing through the pulleys.

The effects which are obtained by rotating the wire guide tube instead of the core pin in the case of covering electrical wires will become more apparent from the following description.

The liquid lubricant is removed from the extruded tube in the unsintered state. The outer surface of the tube is heated to a temperature of 327° C under atmospheric pressure. Before it is cooled below 327° C, the pressure applied to the outer surface of the tube is decreased so that there is a pressure differential between the outer and inner surface of the tube. This difference in pressure causes the tube to expand to a predetermined inside diameter. The tube is then cooled below 327° C with the pressure difference maintained. A quality stable thermally contractive tube is thus produced.

Even if the temperature of the ptfe resin is increased above 327° C, its molten viscosity remains high. Therefore, it is difficult to expand a resin tube by the difference in pressure described above if the wall thickness is greater than approximately 0.2 mm. Accordingly, in some cases the pressure difference must be increased by applying a pressure higher than the atmospheric pressure to the inner surface of the tube, preferably higher than 0.7 Kg/cm$^2$.

However, it should be noted that the necessary difference in pressure also depends on the diameter of the tube. As the inside diameter is increased, the pressure difference required for the expansion of the tube can be decreased. Therefore, the difference in pressure should be varied according to the inside diameter of the tube.

A conventional unsintered tube cannot withstand an internal pressure of 0.7 Kg/cm$^2$, and will burst at a pressure much lower than this. This phenomenon also depends on the inside diameter and wall thickness of the tube. For instance, a tube having a 0.5 mm wall thickness and 6 mm in inside diameter cracked at an internal pressure of about 0.3 Kg/cm$^2$. However, a similarly dimensioned tube obtained by rotating at least one of the mandrel and the die withstood an internal pressure on the order of 1 Kg/cm$^2$, which is clear evidence that tubes extruded by rotating the metal walls of the extruder are much stronger.

FIG. 5 is a schematic side view showing an apparatus for practicing the process of this invention.

A tube 31 coiled around a supply bobbin 30 is fed through a heating furnace 33 at a constant speed by a driving capstan 32. The tube 31 leaves the heating furnace 33 at a temperature above 327° C and is introduced into a vacuum case 34 for radial expansion at a sufficiently high speed that the temperature of the tube does not fall below 327° C. The reduced pressure in the vacuum case 34 is maintained by a control valve 36 while the vacuum case is evacuated through a pipe 35 connected to a vacuum pump (not shown). The vacuum case 34 is equipped with an air inlet pipe 37 and an outlet pipe 38 for passing air therethrough for cooling the tube below 327° C immediately after the tube is radially expanded, and the cooling rate is controlled by a valve 39. To maintain the vacuum case 34 at a reduced pressure, sealing dies 40 and 42 are provided on the inlet and outlet ends of the vacuum case, respectively.

The radially expanded, cooled, and crystallized tube is coiled around a take-up reel 44 by a driving capstan 43. A rotary force is applied from the same driving motor (not shown) to both of the driving capstans 32 and 43 to rotate them at the same speed, whereby the tube is longitudinally fixed. The tube is also radially fixed by the evacuation force in the vacuum case 34, whereby the expansion and shrinkage of the tube are prevented.

Since, with only the evacuation force in the vacuum case 34, the pressure difference between the inside and the outside surfaces of the tube 31 may be too low to cause radial expansion, a connecting tube 45 penetrates a rotary joint 46 and the end of the tube 31 so that an inner pressure higher than atmospheric can be introduced into and maintained in the tube by controlling the air pressure from a high pressure source 47 by a regulating valve 48.

Figure 6:
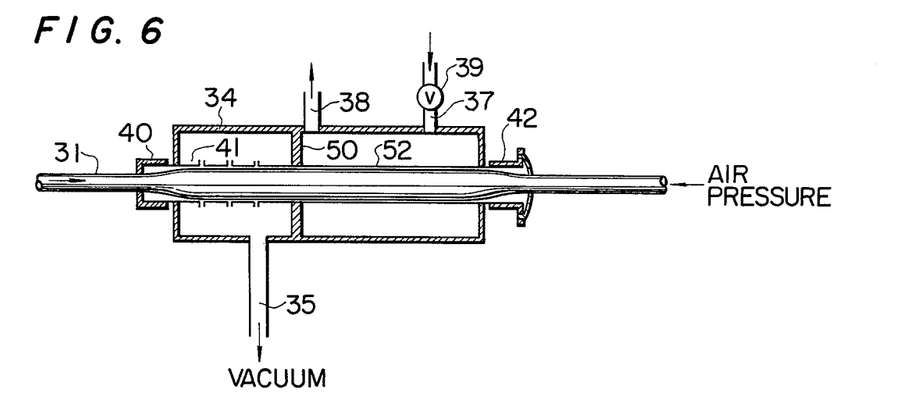
FIG. 6 shows a sectional elevation of the vacuum case 34 of FIG. 5.

FIG. 6 is a sectional elevation of the vacuum case 24. The heated tube 31 enters through the sealing die 40. To insure a good seal the die opening is formed so that its diameter coincides with the outer diameter of the heated tube 31. To reduce the frictional force and prevent any decrease in the driving speed of the capstans thereby, the thickness of the die sealing edges should be less than 3 mm., and preferably about 1 mm. The tube then enters a radial expansion pipe 41 evacuated through a plurality of small holes therein, whereby the tube expands in the radial direction until it outer surface comes into close contact with the inner wall of the pipe. The inner surface of the pipe 41 is sufficiently smooth so that the tube does not contact it too closely, to thereby reduce the stretching of the tube by the driving capstans. The tube expansion section of the vacuum case is connected, through a heat insulating partition wall 50, to a cooling section for crystallizing the tube after expansion.

Since the tube 31 shrinks radially to some extent when being cooled below 327° C in the cooling pipe 52, a space forms between the cooling pipe and the tube. Such a space is helpful in reducing friction, however, and finally the cooled tube exits through the outlet sealing die 42.

Figure 7:
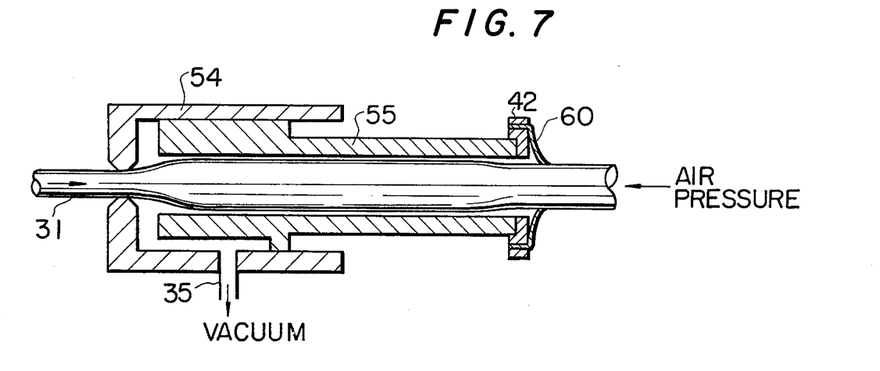
FIG. 7 shows a sectional elevation of a slit type vacuum case.

FIG. 7 is a cross sectional view of a slit type vacuum case 34. The tube 31 enters the vacuum chamber through a sealing die mounted on the inlet portion of an outer frame 54, and the tube is expanded into close contact with the inside surface of an expansion pipe 55. The expansion pipe is cooled by the surrounding air. The radial expansion pipe 55 is slidable within the outer frame 54 to vary the volume of the vacuum chamber, whereby the latter can be set at an optimum length to rapidly expand the tube without breaking it.

A rubber diaphragm 60 is mounted on the sealing die 42 at the outlet end of the vacuum case to prevent air leakage into the case. The vacuum chamber length/volume must be adjusted according to the diameter, wall thickness, temperature, and travelling speed of the tube 31.

EXAMPLE 1

Three (3) Kg of Polyflon F-104 made by Daikin Kogyo Co. was mixed with 0.84 Kg of white oil (Smoil P-55 made by Muramatsu Sekiyo Co.). The mixture was extruded into a tube using a ram type extruder with an inside cylinder diameter of 90 mm, a mandrel 16 mm in outside diameter, a core pin 4.0 mm in outside diameter, and a die 5.5 mm in inside diameter.

The die and the die-insert were heated at 40° C and 90° C, respectively. The extrusion was carried out at a rate of 1.0 m/min by rotating the mandrel and the core pin clockwise to obtain a tube having a uniform wall thickness. After the white oil was removed from the tube by trichloroethylene extraction, the tube was expanded by the apparatus shown in FIG. 5. The temperature of the heating furnace was 560° C, the tube feed rate was 95 cm/min, the internal pressure of the tube was 0.75 Kg/cm$^2$, and the vacuum drawn was 6 to 8 cmHg.

When the sealing die and outlet openings were set at 5.6 mm and 4.0 mm, respectively, and the inside diameter of the radial expansion pipe was 12.0 mm, the expanded tube was 11.2 mm in inside diameter and 0.34 mm in wall thickness. Upon heating at 350° C, this tube contracted by less than 6% in the longitudinal direction while its inside diameter contracted to 4.1 mm. When core materials were covered with the tubes and heated to 350° C, no cracks were generated in the longitudinal direction, and in all of the test pieces, complete adhering and covering were observed.

For comparison, tubes available on the market were applied to and tested with the same core materials. Eight of the test pieces cracked, and two of them developed cracks over 3 cm long.

EXAMPLE 2

The same unsintered tube as in Example 1 was expanded with a heating furnace temperature of 510° C, a feed rate of 25 cm/mn, an internal tube pressure of 1.4 Kg/cm$^2$, a vacuum of 10 cmHg, and the inside diameter of the expansion pipe was 15.0 mm. The expanded and cooled tube was 14.2 mm in inside diameter and 0.21 mm in wall thickness. When it was heated to 345° C, it contracted less than 3% in length while its diameter contracted to 4.2 mm.

EXAMPLE 3

By varying the rotational speeds and the temperatures of the die and the mandrel, pipes were extruded under conditions similar to those in Examples 1, and the tubes were expanded with a heating furnace temperature of 560° C, a feed rate of 95 cm/min, and an expansion pipe inside diameter of 12.0 mm. The internal and external (vacuum) pressures were also varied. The results of example 3 are shown in Table 1:

Table 1

| Test No. | Extruding condition | | | | Expanding condition | | Results | | |
|---|---|---|---|---|---|---|---|---|---|
| | Temperature | | Revolution | | Tube internal pressure | Vacuum degree | I.D. | Wall thickness | Longitudinal contraction percentage |
| | Die | Die-insert | Die-insert | Mandrel | | | | | |
| | °C | °C | rpm | rpm | Kg/cm$^2$ | cmHg | mm | mm | % |
| 1 | | | | | 1.2 | 9–12 | 11.4 | 0.29 | 4 |
| 2 | 30 | 90 | 40 | 80 | 0.7 | 10–15 | 10.6 | 0.32 | 3 |
| 3 | | | | | 0 | 7–10 | 5.2 | 0.68 | 1 |
| 4 | | | | | 1.0 | | Burst. | Could not measure. | |
| 5 | 40 | 60 | 40 | 60 | 0.7 | 7–9 | 11.2 | 0.30 | 6 |
| 6 | | | | | 0.3 | 10–12 | 6.0 | 0.55 | 7 |
| 7 | | | 0 | 85 | 1.2 | 9–15 | 10.8 | 0.29 | 4 |
| 8 | 40 | 110 | 0 | 75 | 1.2 | 8–13 | 11.4 | 0.28 | 3 |
| 9 | | | 0 | 65 | 1.2 | 10–15 | 11.4 | 0.30 | 4 |
| 10 | | | 0 | 55 | 1.2 | | Burst. | Could not measure. | |
| 11 | | | 0 | 55 | 1.0 | 9–12 | 10.2 | 0.32 | 6 |
| 12 | | | 0 | 22 | 1.0 | | Burst. | Could not measure. | |
| 13 | | | 0 | 22 | 0.7 | 15–20 | 10.4 | 0.30 | 10 |

Table 1-continued

| Test No. | Extruding condition Temperature Die | Extruding condition Temperature Die-insert | Extruding condition Revolution Die-insert | Extruding condition Revolution Mandrel | Expanding condition Tube internal pressure | Expanding condition Vacuum degree | Results I.D. | Results Wall thickness | Results Longitudinal contraction percentage |
|---|---|---|---|---|---|---|---|---|---|
| Comparison | | | | | | | | | |
| 1 | | | 0 | 0 | 0.7 | | Burst. | Could not measure. | |
| 2 | 40 | 110 | 0 | 0 | 0.4 | 9-15 | 6.3 | 0.65 | 15 |
| 3 | 40 | 40 | 0 | 0 | 0.4 | | Burst. | Could not measure. | |
| 4 | | | 0 | 0 | 0.2 | 7-12 | 4.3 | 0.16 | 18 |

As may be seen from the results tabulated in Table 1, when the die-insert and the mandrel rotate at the same speed, the internal pressure of the tube can be increased while keeping the temperatures of the die and the die-insert high and increasing the temperature differential therebetween. Under such conditions the tube can be stably expanded. Given these same temperature conditions, the internal tube pressure can be increased as the r.p.m. is increased.

When all rotation is suspended, the internal tube pressure is decreased and it is difficult to obtain stable expansions.

These results coincide with the frequency of occurrence of cracks when the expanded tubes are heated to 350° C and contracted, and when the tubes are contracted or shrunk on a core material in such a maner that a residual stress is caused.

What is claimed is:

1. A method of manufacturing a thermall contractive tube of a desired diameter from a polytetrafluoroethylene resin, comprising the ordered steps of:
   a. extruding a mixture of liquid lubricant and tetrafluoroethylene resin to form an unsintered tube;
   b. removing said lubricant;
   c. heating said unsintered tube to a temperature higher than 327° C under atmospheric pressure;
   d. immediately after the heating step, and while the tube temperature is still above 327° C, reducing the pressure applied to the outer surface of the tube to provide a pressure differential between the inner and outer surfaces of the tube sufficient to thereby radially expand the tube to said desired diameter: and
   e. cooling the tube to a temperature below 327° C while maintaining the pressure differential.

2. A method as claimed in claim 1, further comprising the step of applying a pressure greater than 0.7 Kg/cm$^2$ to the inner surface of the tube to assist the radial expansion thereof.

3. A method as claimed in claim 1, wherein the unsintered tube formed by the extrusion step has a fibrous structure, the direction of orientation of the fibrous structure having a lateral component perpendicular to the extrusion direction.

4. A method as claimed in claim 2, wherein the unsintered tube formed by the extrusion step has a fibrous structure, the direction of orientation of the fibrous structure having a lateral component perpendicular to the extrusion direction.

5. A method as clamed in claim 1, wherein the tube is surrounded by a fixed diameter jacket during the radial expansion and cooling steps to thereby limit the radial expansion of the tube.

6. A method as claimed in claim 2, wherein the tube is surrounded by a fixed diameter jacket during the radial expansion and cooling steps to thereby limit the radial expansion of the tube.

7. A method as claimed in claim 3, wherein the tube is surrounded by a fixed diameter jacket during the radial expansion and cooling steps to thereby limit the radial expansion of the tube.

8. A method as claimed in claim 4, wherein the tube is surrounded by a fixed diameter jacket during the radial expansion and cooling steps to thereby limit the radial expansion of the tube.

9. A method as claimed in claim 1, further comprising the step of heating the outlet nozzle of the extruder, whereby the exit temperature of the extruded tube is higher than that of the mixture.

10. A method as claimed in claim 2, further comprising the step of heating the outlet nozzle of the extruder, whereby the exit temperature of the extruded tube is higher than that of the mixture.

11. A method as claimed in claim 3, further comprising the step of heating the outlet nozzle of the extruder, whereby the exit temperature of the extruded tube is higher than that of the mixture.

12. A method as claimed in claim 4, further comprising the step of heating the outlet nozzle of the extruder, whereby the exit temperature of the extruded tube is higher than that of the mixture.

13. A method as claimed in claim 9, wherein the difference between the exit temperature of the extruded tube and the temperature of the mixture is at least 50° C.

14. A method as claimed in claim 10, wherein the difference between the exit temperature of the extruded tube and the temperature of the mixture is at least 50° C.

15. A method as claimed in claim 11, wherein the difference between the exit temperature of the extruded tube and the temperature of the mixture is at least 50° C.

16. A method as claimed in claim 12, wherein the difference between the exit temperature of the extruded tube and the temperature of the mixture is at least 50° C.

17. A method as claimed in claim 3, wherein the fibrous structure is directionally oriented by effecting relative rotation between an axial mandrel of the extruder and an outlet nozzle of a die thereof during extrusion, said axial mandrel having a smooth surface tapering from a large diameter approximately equal to the inside diameter of the extruded tubing material, said die having a smooth inner surface tapering from a cylinder to a relatively smaller diameter at said nozzle approximately equal to the outside diameter of the extruded tubing material.

18. A method as claimed in claim 4, wherein the fibrous structure is directionally oriented by effecting relative rotation between an axial mandrel of the extruder and an outlet nozzle of a die thereof during extrusion, said axial mandrel having a smooth surface tapering from a large diameter approximately equal to the inside diameter of the extruded tubing material, said die having a smooth inner surface tapering from a cylinder to a relatively smaller diameter at said nozzle approximately equal to the outside diameter of the extruded tubing material.

19. A method as claimed in claim 8, wherein the fibrous structure is directionally oriented by effecting relative rotation between an axial mandrel of the extruder and an outlet nozzle of a die thereof during extrusion, said axial mandrel having a smooth surface tapering from a large diameter approximately equal to the inside diameter of the extruded tubing material, said die having a smooth inner surface tapering from a cylinder to a relatively smaller diameter at said nozzle approximately equal to the outside diameter of the extruded tubing material.

20. A method as claimed in claim 16, wherein the fibrous structure is directionally oriented by effecting relative rotation between an axial mandrel of the extruder and an outlet nozzle of a die thereof during extrusion, said axial mandrel having a smooth surface tapering from a large diameter approximately equal to the inside diameter of the extruded tubing material, said die having a smooth inner surface tapering from a cylinder to a relatively smaller diameter at said nozzle approximately equal to the outside diameter of the extruded tubing material.

* * * * *

UNITED STATES PATENT AND TRADEMARK OFFICE
CERTIFICATE OF CORRECTION

PATENT NO. : 4,104,394

DATED : August 1, 1978

INVENTOR(S) : Koichi OKITA

It is certified that error appears in the above-identified patent and that said Letters Patent are hereby corrected as shown below:

IN THE HEADING:

Foreign Application Priority Data:

Delete "Sep. 11, 1976" - Insert -- Nov. 9, 1976 --

Signed and Sealed this

Twenty-seventh Day of February 1979

[SEAL]

Attest:

RUTH C. MASON
Attesting Officer

DONALD W. BANNER
Commissioner of Patents and Trademarks